United States Patent
Itou et al.

(10) Patent No.: US 7,434,687 B2
(45) Date of Patent: Oct. 14, 2008

(54) PACKAGE FOR MEDICAL TUBES

(75) Inventors: Yasushi Itou, Fujinomiya (JP); Jun Iwami, Fujinomiya (JP); Shigeki Numata, Fujinomiya (JP)

(73) Assignee: Terumo Kabushiki Kiasha, Shibuya-Ku, Tokyo (JP)

( * ) Notice: Subject to any disclaimer, the term of this patent is extended or adjusted under 35 U.S.C. 154(b) by 441 days.

(21) Appl. No.: 11/179,505

(22) Filed: Jul. 13, 2005

(65) Prior Publication Data

US 2006/0011501 A1 Jan. 19, 2006

(30) Foreign Application Priority Data

Jul. 14, 2004 (JP) ............................. 2004-207711

(51) Int. Cl.
*B65D 83/10* (2006.01)

(52) U.S. Cl. .................. 206/370; 206/363; 206/438

(58) Field of Classification Search ................ 206/363, 206/364, 370, 438, 439, 570; 604/163, 171, 604/263, 533; 53/449, 469
See application file for complete search history.

(56) References Cited

U.S. PATENT DOCUMENTS

| 4,925,448 A | | 5/1990 | Bazaral |
|---|---|---|---|
| 5,131,537 A | * | 7/1992 | Gonzalez .................... 206/364 |
| 5,163,554 A | | 11/1992 | Lampropoulos et al. |
| 5,501,341 A | * | 3/1996 | Van Es ....................... 206/364 |
| 5,947,296 A | | 9/1999 | Castora |

OTHER PUBLICATIONS

European Search Report dated Oct. 31, 2005.

* cited by examiner

*Primary Examiner*—David T Fidei
(74) *Attorney, Agent, or Firm*—Buchanan Ingersoll & Rooney PC (57) ABSTRACT

A package for medical tubes allows a plurality of medical tubes, which are to be used for a surgical procedure such as a catheter surgical operation, to be primed at the same time. The package holds a plurality of medical tubes in a condition in which the medical tubes are individually connected to a branching member.

26 Claims, 7 Drawing Sheets

PACKAGE FOR MEDICAL TUBES

This application is based on and claims priority under 35 U.S.C. § 119 with respect to Japanese Application No. 2004-207711 filed on Jul. 14, 2004, the entire content of which is incorporated herein by reference.

FIELD OF THE INVENTION

This invention generally relates to a package for accommodating medical tubes. More specifically, the present invention pertains to a package in which are accommodated medical tubes used for a surgical procedure such as a diagnosis or a medical treatment in which a medical tube such as a catheter is used.

BACKGROUND DISCUSSION

A surgical operation or procedure such as a diagnosis or a medical treatment in which a catheter is used has been popularized because it imposes a comparatively low burden on a patient. Such a surgical operation as just mentioned is performed by introducing various instruments beginning with a catheter into a puncture hole or the like formed in an arm, a leg or other site of the patient and extending to an artery. Further, during a surgical procedure, a condition in the blood vessel of the patient is observed on an X-ray contrast image. More particularly, the patient lies on an imaging intensifier, which is a light receiving apparatus which receives X-rays to produce an image, and X-rays are irradiated on the patient from above.

In a surgical procedure such as that described above, a wide variety of medical devices and drugs are used, perhaps involving up to several tens of medical devices and drugs, including throwaway unwoven fabrics (drapes) adapted to be spread on an imaging intensifier, devices and drugs such as an antiseptic used at a preparation stage prior to a surgical procedure (such as a set for drip fusion including a needle and a tube for dripping the heparin of an antithrombotic drug to a patient), surgical gowns for doctors, absorbent cottons, tweezers, forceps and scissors for applying antiseptic, skin cutting surgical knives used after a surgical operation is started, indwelling needles, introducer sheaths and dilators, guide wires for the introducer, syringes, angiographic catheters, guide wires for the angiographic catheter, angiographic agent, microcatheters and so forth which are used for a diagnosis or a medical treatment, PTCA (Percutaneous Transluminal Coronary Angioplasty) guiding catheters (shape for the right side of the heart, shape for the left side and so forth), PTCA guide wires, PTCA balloon catheters, balloon dilating devices (indeflators), stent delivery catheters, hemostatic devices used after an operation or procedure, and beakers, cups and so forth for temporarily keeping various drugs and agents. To help prevent infection, most of these medical devices, drugs and the like are of the throwaway type.

Conventionally, devices such as those described above are prepared by being placed on a table in advance by a nurse. However, because the nurse does not disinfect as carefully as a doctor, the nurse is typically not permitted to touch devices which may directly come in contact with the blood of a patient. Accordingly, somewhat complicated operations or procedures are carried out such as remotely taking out the device from a package using forceps or the like. Also a supplying operation for purchasing and preparing such a great number of devices is quite complicated.

In such a situation as described above, there is a trend that devices for use with a catheter in a surgical operation or procedure are enveloped in a tray or the like to form a kit, thus simplifying the labor associated with purchasing and disposition, while also inhibiting or preventing errors in use and errors in preparation. An example of a package intended to achieve such results is disclosed in U.S. Pat. No. 5,947,296.

Medical devices such as catheters that are elongated in form and adapted to be inserted into the blood vessel of a human being require certain precautionary measures. For example, to prevent air from being admitted into the blood vessel of the human being during use, it is necessary to inject a fluid such as saline (physiological salt solution) or other appropriate fluid into the lumen (the operation is called priming) of the medical device before the device is used. The package disclosed in the aforementioned U.S. Pat. No. 5,947,296 is configured to accommodate a plurality of catheters. However, it is still necessary to carrying out the priming operation by injecting fluid (saline) into the catheters one by one. It would this be desirable to provide a package and method which are not as susceptible to such shortcomings.

SUMMARY

According to one aspect, a package for medical tubes comprises a holder having an aseptic interior in which is positioned a plurality of medical tubes, with each of the medical tubes comprising a tube body possessing a tube wall defining a lumen extending between a distal end portion of the medical tube and a proximal end portion of the medical tube. In addition, a branching member is provided to which is connected each of the plurality of medical tubes. The branching member comprises a plurality of branched flow paths each fluidly communicating with the lumen of one of the plurality of medical tubes.

In accordance with another aspect, a package for medical tubes comprises a holder possessing an interior under aseptic conditions, and a plurality of medical. tubes positioned in the interior of the holder, with each of the plurality of medical tubes comprising a tube body possessing a distal end portion, a proximal end portion, and a tube wall surrounding a lumen that extends between the distal end portion and the proximal end portion. In addition, a branching member is positioned in the interior of the holder and comprises a plurality of flow paths each adapted to be fluidly connected to the lumen of one of the medical tubes to fluidly communicate the flow path with the lumen of the medical tube. The branching member also comprises a main adapter adapted to fluidly communicate with the plurality of flow paths so that priming fluid introduced into the main adapter can flow to the flow paths and into the lumen of each medical device that has been fluidly connected to one of the flow paths.

According to another aspect, a package for medical tubes comprises a tray having a bottom and an upstanding peripheral wall, a cover sealed to the tray to define together with the bottom and the upstanding peripheral wall an aseptic interior, a plurality of medical tubes positioned in the aseptic interior of the tray, and a branching member positioned within the aseptic interior of the tray. Each of the plurality of medical tubes comprises a tube body possessing a distal end portion, a proximal end portion, and a tube wall surrounding a lumen that extends between the distal end portion and the proximal end portion. The branching member comprises a plurality of flow paths each fluidly connected to the lumen of a respective one of the medical tubes to fluidly communicate each flow path with the lumen of the respective medical tube.

The medical tubes may include an angiographic catheter, a PTCA guiding catheter, an introducer sheath, a dilator or a guide wire holder tube. In addition, each of the medical tubes may have a connector connected to the branching member.

Preferably, each of the branched flow paths connected individually to the medical tubes has an orifice defining an inner diameter of the flow path, with the flow path sectional area of each of the orifices being smaller than the sectional area of that one of the lumens of the medical tubes which has the smallest sectional area. Further, it is preferable that the flow path sectional area of each of the orifices increases in proportion to the volume when fluid is injected into the lumen of the corresponding medical tube and is smaller than the sectional area of that one of the lumens of the medical tubes which has the smallest sectional area.

A further aspect pertains to a method for priming a plurality of medical tubes. The method comprises introducing fluid from a fluid source into a branching member that is connected to a plurality of medical tubes, wherein the branching member comprises a plurality of branched flow paths and each of the plurality of medical tubes comprises a tube wall surrounding a lumen. Each branched flow path of the branching member is in fluid communication with the lumen of one of the plurality of medical tubes, and the fluid introduced into the branching member flows to the plurality of branched flow paths and into the lumen of each of the medical tubes to fill the lumen of each of the medical tubes with the fluid.

The foregoing and additional features and characteristics associated with the subject matter described herein will become more apparent from the following detailed description, considered together with the accompanying drawing figures in which like parts or elements are denoted by like reference symbols.

DETAILED DESCRIPTION

Figure 1:
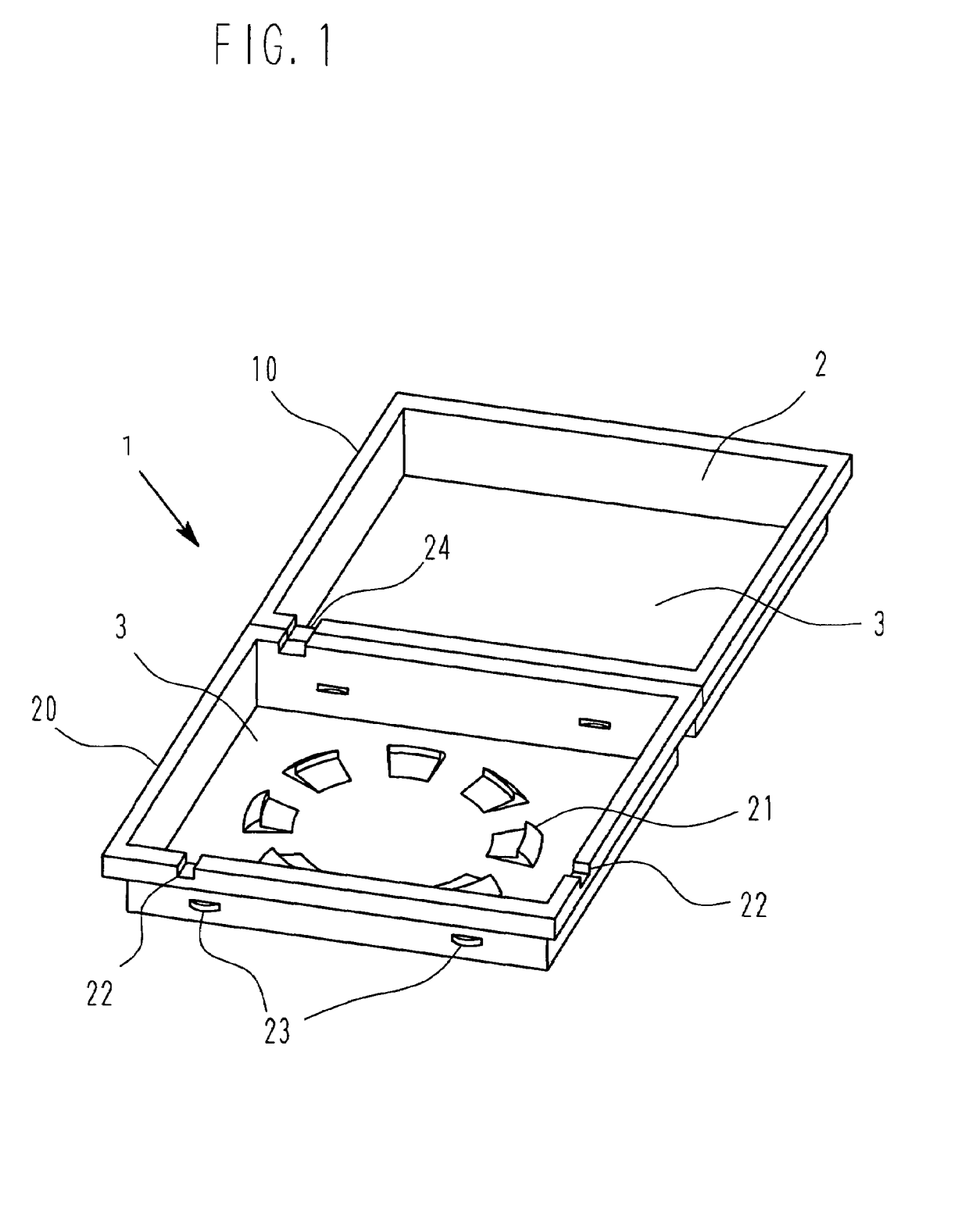
FIG. 1 is a perspective view of a medical device accommodating tray according to an embodiment of the present invention.

The following detailed description describes packages for medical devices such as medical tubes according to embodiments of the present invention. FIG. 1 illustrates an overall tray 1 forming a holder of a medical device package.

As shown in FIG. 1, the overall tray 1 includes a first tray 10 and a second tray 20 joined together. In the illustrated version, the two trays 10, 20 are joined together along the lengthwise sides of the trays 10, 20. Each of the trays 10, 20 can be configured to possess a bottom surface surrounded by an upstanding peripheral wall. In the illustrated embodiment, the bottom surface is defined by a bottom wall or plate 3 that is four-sided and possesses a rectangular shape, having one pair of opposing sides approximately 30 to 70 cm in length and the other pair of opposing sides approximately 20 to 60 cm in length. In the illustrated embodiment, the upstanding peripheral wall is formed by four walls 2 which may possess a height of 3 to 20 cm.

Catheters and other devices to be inserted into a blood vessel such as sheaths and guide wires need be dipped at both inner and outer surfaces thereof in saline before they are used. With the general construction of the trays 10, 20 described above, the trays 10, 20 can be filled with a suitable amount of saline as will be mentioned in more detail below. In particular, by providing the trays 10, 20 with upstanding walls 2, the trays 10, 20 are able to reserve or contain the saline therein. While the dimensions of the trays described above are not necessarily limiting, trays possessing dimensions such as those generally described above are economical in that they are not excessively large in size and thus do not require an excessively large amount of saline. Further, if the trays 10, 20 are excessively large in size, it is inconvenient to dispose of them after use.

The bottom wall 3 of the tray 20 has a plurality of upstanding projections 21 disposed along a circle. The projections 21 serve to suppress or hold down devices like guide wires packaged in a circular form so as not to move upon packaging. Since the guide wires generally have a form in which a thin elongated wire material (e.g., superelastic alloy) is coated with a resin material, even if they are deformed, they are less likely to maintain such deformation and can thus be packaged in a rounded or curved form. Further, the tray 20 is injected with the saline upon operation and is used to dip angiographic catheters and guide wires into the saline. The projections 21 can also serve to partition or keep separate the medical devices (e.g., catheters and guide wires) upon dipping in the saline to help avoid situations in which the medical devices become mixed with each other and cannot individually be taken out readily. Further, each of the projections 21 is shaped such that a substantially vertical wall is formed on the inner side thereof and a moderately inclined face is formed on the outer side thereof. Consequently, a guide wire having a high elasticity can be prevented from shifting out to the outer side of the projections 21 and can be placed readily on the fingers of an operator when it is taken out. Also, the taking out of a catheter is advantageously facilitated.

Since the projections 21 are spaced apart from one another so as to define cutaways or spaces between the projections 21 generally arranged in a circular fashion, it is possible for users' fingers to touch or grasp the guide wire through the cutaway portions and take out the guide wire readily. This may be particularly helpful when, for example, a guide wire is disposed on the inner side of the circuit and is biased to the inner circumference side of the projections. The spaces between the projections permit access to the guide wire and allow the guide wire to be taken out readily from the projection.

Further, since the projections 21 are provided in the inside of the tray, when the saline is introduced into the tray, the volume taken up by the projections means that a lesser amount of saline is required to allow a device to be dipped in the saline than would be the case if the tray possessed a flat bottom with no projections.

Further, a plurality of notches or recesses 22 are provided on the upwardly facing edge of one or more of the upstanding walls 2 extending around the tray periphery. In the illustrated embodiment, a notch or recess is provided on two of the walls 2. The recesses 22 are formed such that a hub at a proximal end portion of a catheter can be attached thereto upon surgical operation. Consequently, a plurality of catheters 100 can be placed, upon operation, in order of use thereof in advance and can be taken out readily. It is to be noted that a different recess or notch 24 is provided such that, when a catheter is packaged in such a manner as hereinafter described, the notch or recess 24 allows the catheter to span between the trays 10, 20.

A plurality of projections 23 are provided at generally central portions of the walls 2 of the tray 20. The projections 23 are adapted to project either toward the interior of the tray or toward the outside of the tray by pushing on the projections with a finger. When the catheters 100 are to be dipped into the saline in the tray 20, the projections 23 are pushed to project to the inner side of the tray 20 to inhibit or prevent the catheters 100 from shifting to the outside of the tray 20 (i.e., to retain the catheters within the tray). Then, when the saline and the medical devices are to be disposed after the operation comes to an end, the projections 23 are pushed to project to the outer side of the tray 20 to change the function thereof so that they do not disturb such disposition.

The trays 10, 20 can be formed by fabrication methods such as vacuum molding, compressed air molding or press molding from a high molecular material having a desired strength such as ABS, AES, PC, PP, PE, PS, HIPS, PET or PVC.

Figure 2:
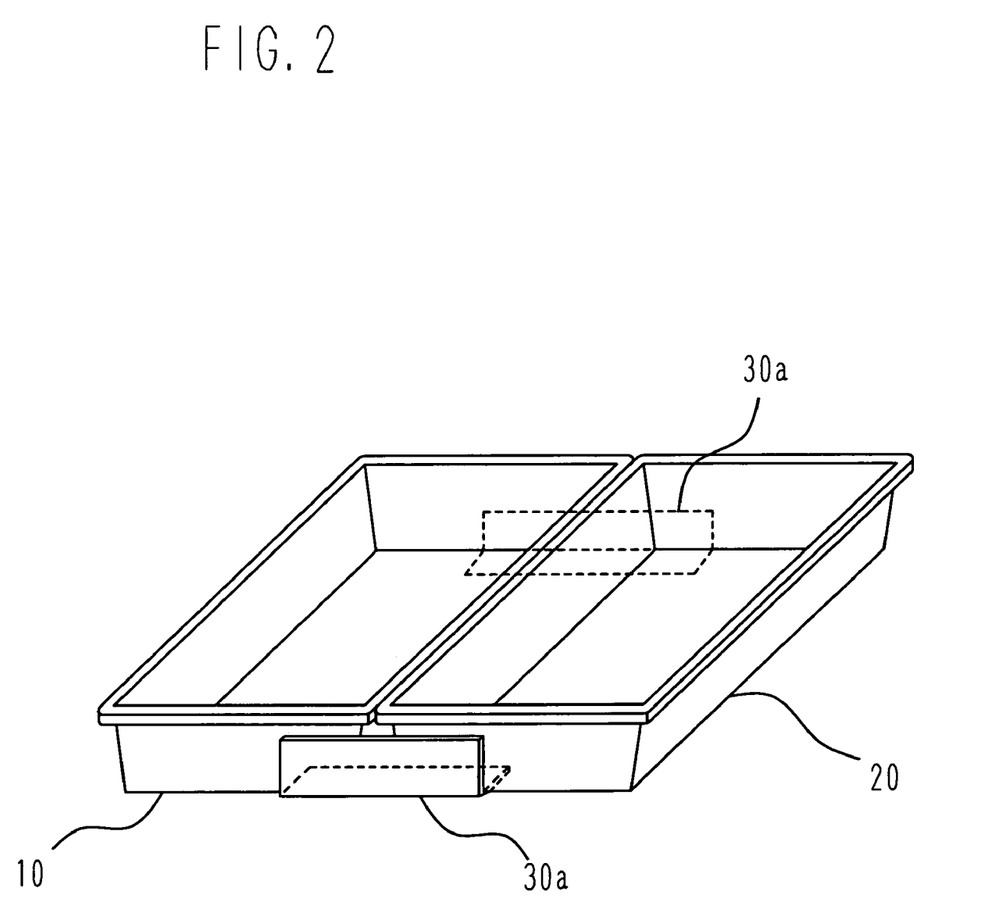
FIG. 2 is a perspective view of a medical device accommodating tray illustrating a manner in which sections of the tray shown in FIG. 1 are joined together.

FIG. 2 shows a manner in which the trays 10, 20 shown in FIG. 1 can be joined together. As shown in FIG. 2, the trays 10, 20 can be secured to each other by fixing members 30. Although a single fixing member 30 may be used by itself, a plurality of such fixing members 30 can be provided to more firmly fix the trays to each other. Each of the fixing members 30 is formed as an L-shaped plate member which contacts closely with bottom and side faces of the two trays 10, 20 which are positioned adjacent each other. The fixing member 30 can be made of a metal material or a hard plastic material. The fixing members 30 are preferably adhered to the side faces and the bottom faces of the trays 10, 20 by way of an adhesive tape or the like to thereby fix the trays 10, 20 firmly to each other so that they are not separated from each other during transportation. An adhesive material such as a double-sided adhesive tape may be adhered to the inner side of the fixing members 30.

Figure 3:
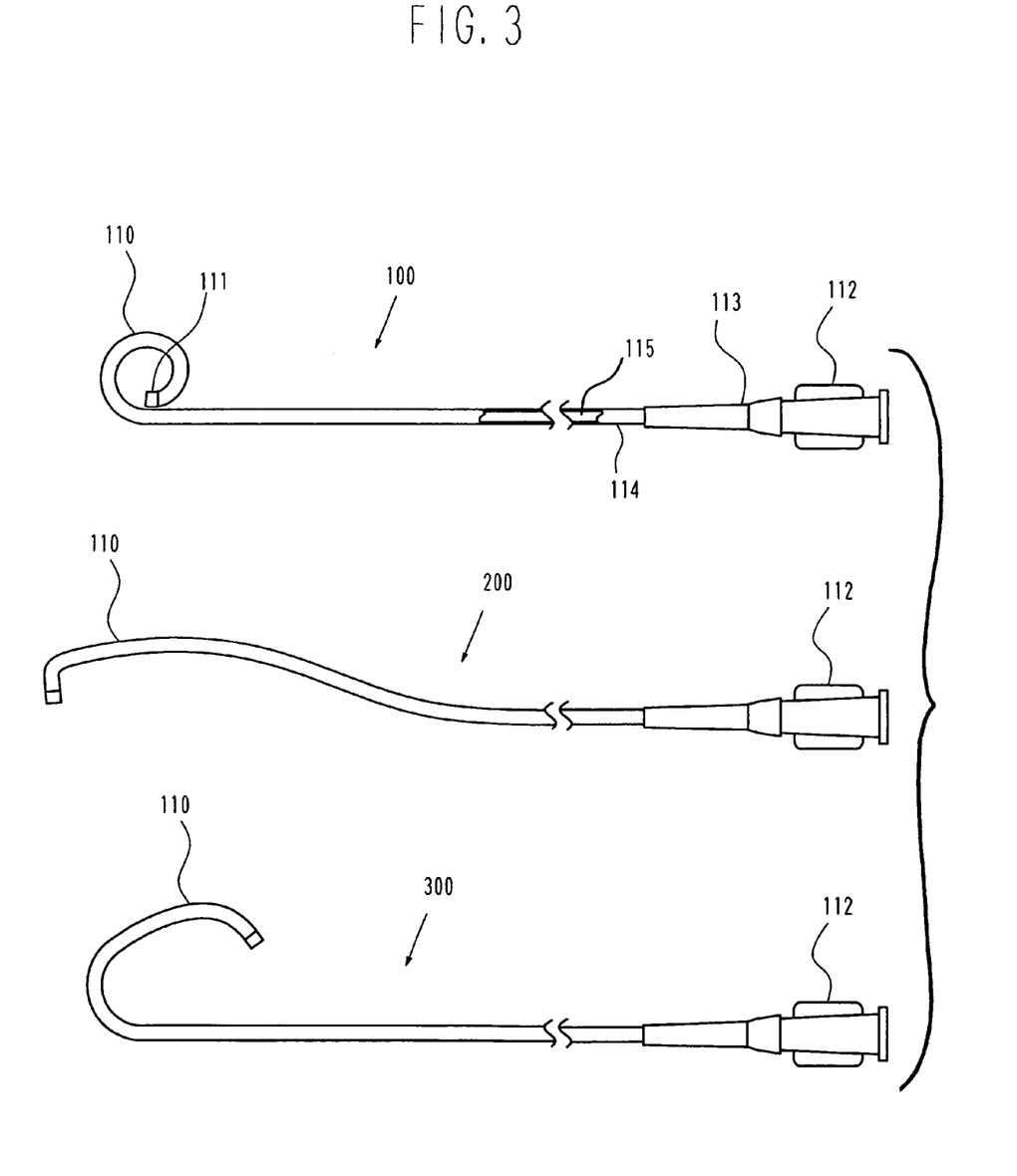
FIG. 3 are perspective views of angiographic catheters.

FIG. 3 illustrates three different angiographic catheters 100, 200, 300 adapted to be packaged together according to one embodiment. The catheter 100 is configured such that it includes a tubular body having a lumen 115 which extends from the distal end portion 110 to the proximal end portion 114. In addition, a connector 112 is provided at the proximal end of the tubular body and communicates with the lumen 115. A kink-withstanding protector 113 for preventing kinking of the catheter is provided at the distal end side of the connector 112. A very flexible distal end chip 111 is provided at the extreme distal end of the catheter 100 to protect the inner surface of a blood vessel.

The catheters 100, 200, 300 have the same configuration, except that the distal ends of the catheters possess different shapes. The end region of the distal end portion 110 to be introduced into a blood vessel has a shape curved in order to assure a relatively high degree of selectivity at a branching portion of a blood vessel upon introduction or in order to efficiently distribute a blood vessel contrast agent (an angiographic agent) for obtaining an X-ray image of a blood vessel under the X-ray radioscopy. The end distal portion of the catheter 100 has a pigtail shape. The pigtail shape is suitable to inject a contrast agent into a wide volume of the left ventricle or the aorta to perform contrast imaging.

The distal end portion of the catheter 200 has a Judkins' right (JR) shape. The JR shape is suitable to contrast-image the right coronary artery of the heart.

The distal end portion of the catheter 300 has a Judkins' left (JL) shape. The JL shape is suitable to contrast-image the left coronary artery of the heart.

Figure 4:
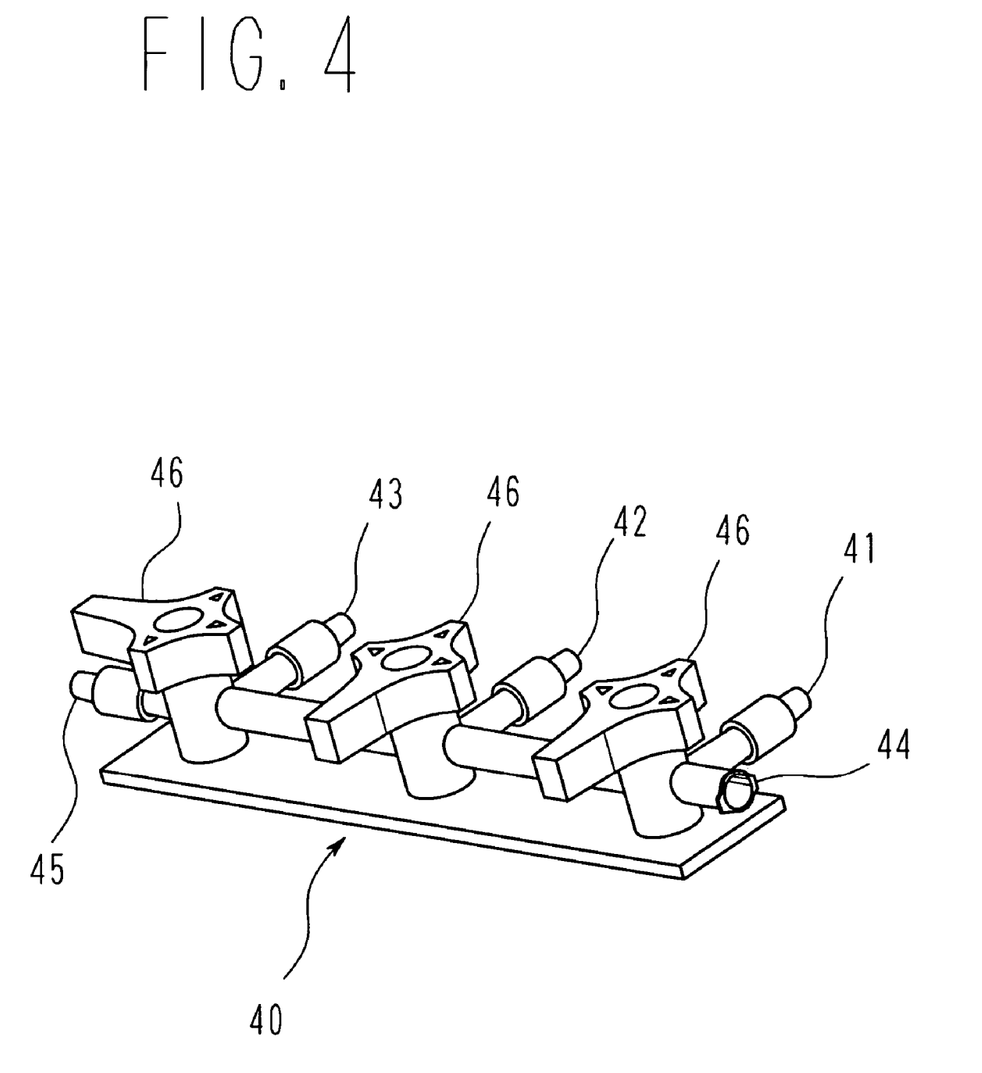
FIG. 4 is a perspective view of a manifold.

FIG. 4 shows a branching member adapted to have a plurality of catheters connected thereto. The branching member is in the form of a manifold 40 capable of being removably connected to the connectors of the catheters 100, 200, 300. The manifold 40 has a plurality of three-way stopcocks and includes a female type main adapter 44 to which a syringe 50 can be connected directly or through a tube, and a plurality of male type adapters 41, 42, 43 having luer locks to which the catheters 100, 200, 300 are to be connected, respectively. In the illustrated embodiment, the number of three-way stopcocks is three, although a different number can be provided to accommodate the intended number of catheters or other medical tubes. Each of the adapters 41, 42, 43 has a three-way stopcock 46 to permit a change in the flow path. More particularly, the rotatable three-way stopcock 46 has projections on all sides and is configured so that fluid does not flow in the direction of the longest (handle) projection of the cock portion of the three-way stopcock 46. A catheter can be attached also to an adapter 45 having a structure similar to that of the adapters 41, 42, 43.

Figure 5:
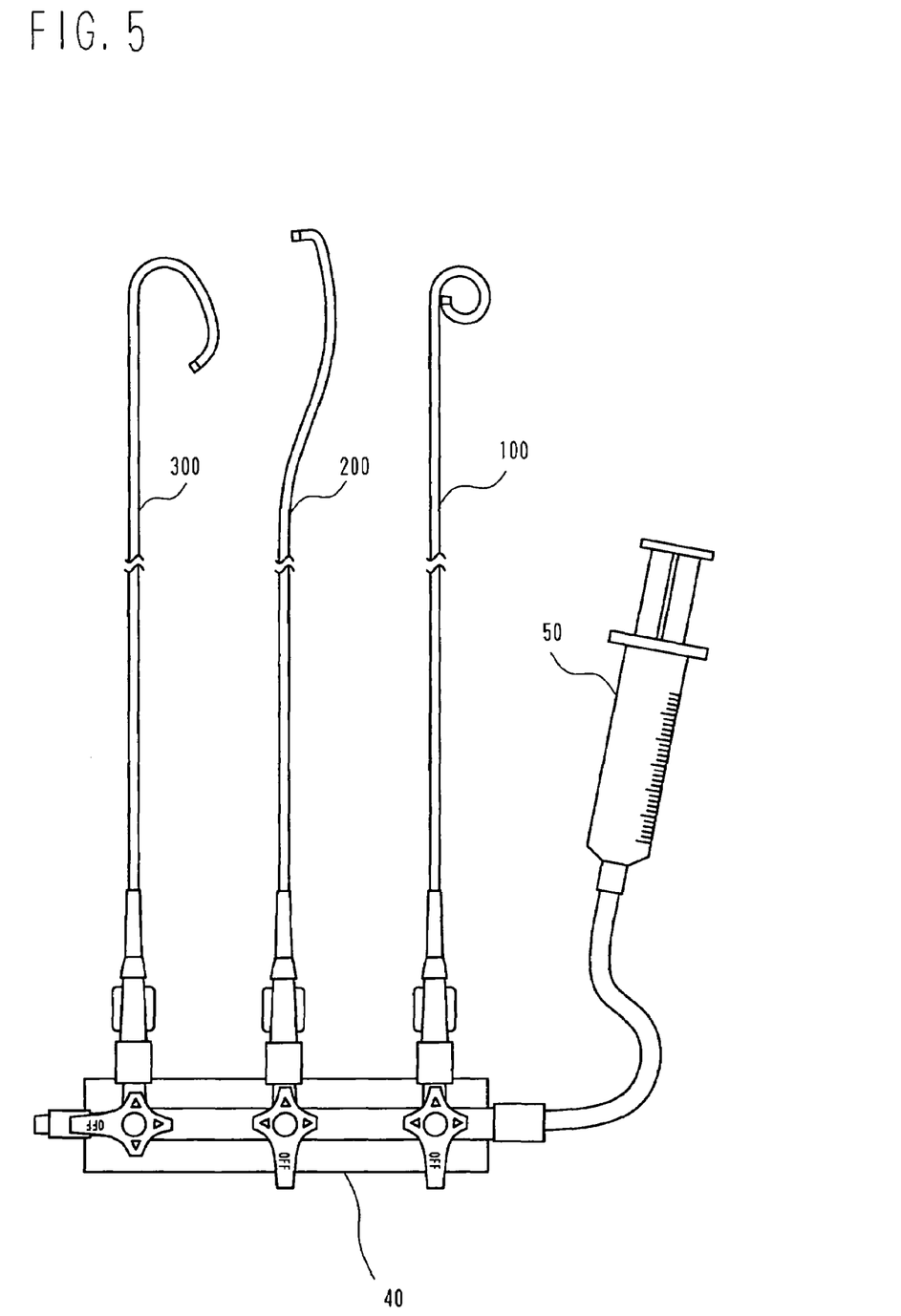
FIG. 5 is a top view illustrating a manner in which medical devices are attached or connected to the manifold.

FIG. 5 shows a single fluid source in the form of a syringe 50 and the catheters 100, 200, 300 connected to the adapters 41-44, respectively. The flow paths of the adapters 41-44 are branched and connected to each other, and when the saline is injected from the syringe 50 into the main adapter 44 in the state shown in FIG. 5, the saline flows into the branched flow paths. Consequently, the three catheters 100, 200, 300 can be primed simultaneously and filled with the saline.

In the embodiments described and illustrated here, since the manifold 40 and the three catheters 100, 200, 300 are aseptically packaged in a mutually connected and integrated relationship with each other, after the aseptic seal of the package is broken and the package is opened(i.e., the cover is removed), the syringe 50 into which the saline is sucked or drawn is connected to the main adapter 44 of the manifold 40. The syringe 50 is then operated to inject the saline. Thus, all three of the catheters can be primed at the same time using only a single operation typically used to prime a single catheter.

After the priming, if the luer lock of any of the adapters 41-43 to which the connectors 112 of the catheters are attached is turned approximately 90 degrees, the catheter can be readily removed from the manifold 40. Therefore, preparations of the catheters can be made very readily in accordance with the order of manipulations.

It is to be noted that the three-way stopcock 46 located on the manifold 40 at a position closer to the main adapter 44 than the other three-way cocks can be used to selectively prime one of the plurality of catheters/medical tubes. Where there is no need for providing the possibility as just described, it is possible to use a manifold which does not include a three-way stopcock.

Figure 6:
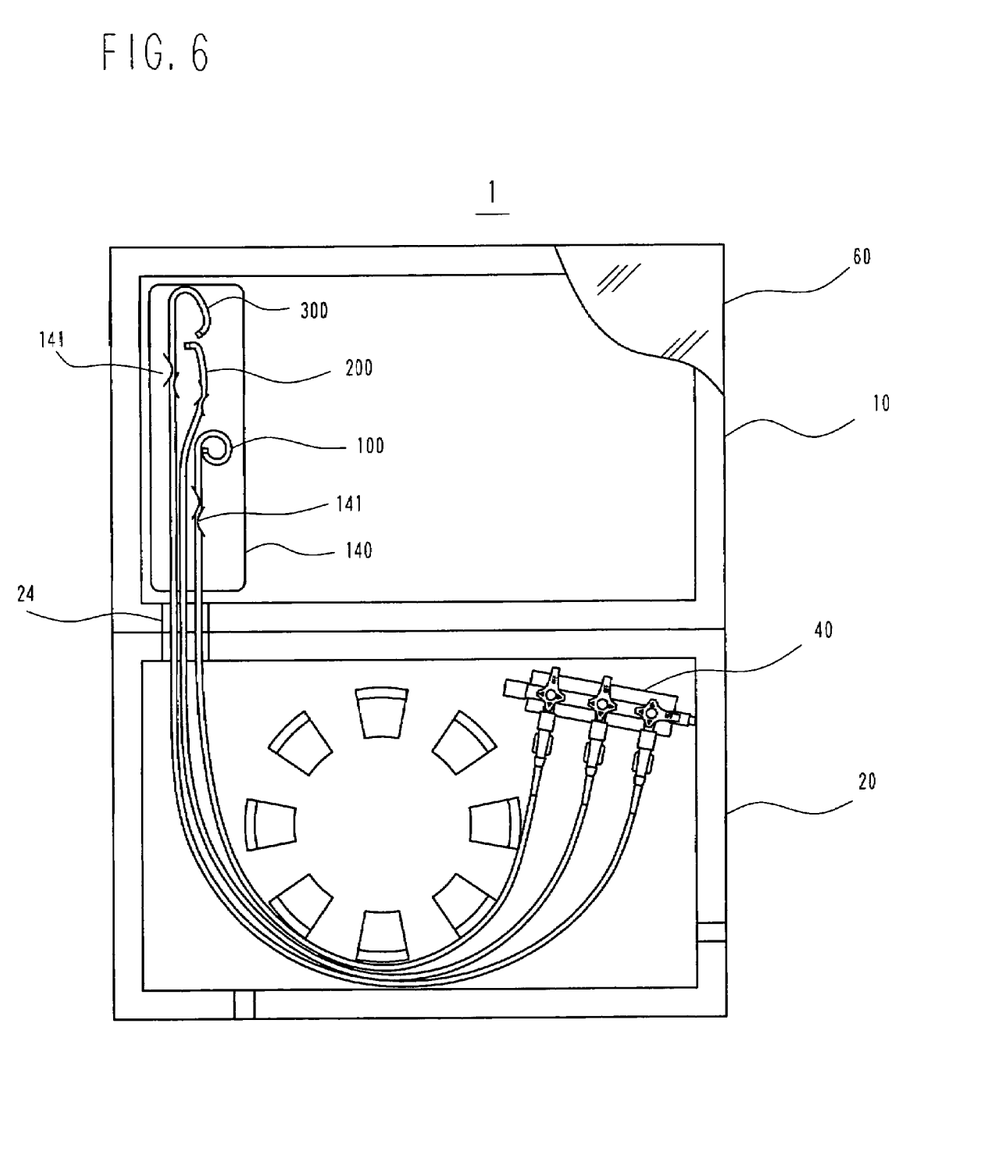
FIG. 6 is a top view illustrating various angiographic catheters disposed in the tray shown in FIG. 1.

FIG. 6 shows a manner in which the catheters 100, 200, 300 attached to the manifold 40 are held interiorly on the tray 1 shown in FIG. 1, with the tray and enclosed catheters 100, 200, 300 (including the attached manifold 40) being aseptically wrapped by a cover or seal 60 that is sealed to the tray to provide the aseptic package. Upon disposition on the tray 1, the distal end portion of each catheter (a 10 cm to 50 cm portion at the distal end of each catheter) is preferably held in a linearly extending state to keep the end shape and maintain the operability such as a torque transmission performance. To this end, the linearly held portion is preferably disposed such that it extends along a wall of a short side of the tray 10.

Further, a portion of the proximal end side of the catheter 100 (a 10 cm to 100 cm portion on the proximal end side of the catheter) is disposed in a curved state so that it may be held in the tray 20. The diameter of the curve preferably remains within a range of 10 cm to 50 cm. When the diameter of the curve is significantly greater than 50 cm, the size of the tray becomes unfavorably large. However, when the diameter of the curve is significantly smaller than 10 cm, the catheter or medical tube may undesirably maintain its bent shape after removal from the tray. A portion of the catheter 100 which spans between the trays 10, 20 is disposed in the recess 24 formed on the wall 2.

As seen in FIG. 6, upon packaging, the catheters 100, 200, 300 are held by a catheter protective sheet 140. Since each catheter has a relatively small diameter allowing it to be inserted into a blood vessel, and is also flexible, the catheters may not possess significant properties allowing the catheters to withstand breaking or bending. It is thus desirable to protect the catheters so that they to not become broken by some other device enclosed in the tray 1 during transportation. The catheter protective sheet 140 can be in the form of a sheet of synthetic resin material and possesses cuts 141 providing retaining portions that retain the distal end portions of the catheters in place.

The embodiment described above involves the packaging of angiographic catheters. However, the invention is not limited in this regard and can be applied to other kinds of medical tubes requiring priming, including medical tubes used together in a single surgical operation. For example, an introducer sheath 500, a dilator 510 for the introducer sheath 500, a guide wire holder tube 520, and guiding catheters for which a plurality of catheters having different distal end shapes similar to the angiographic catheters described above can be packaged together. The introducer sheath 500 is used as an entrance portion for introducing various kinds of catheters into a blood vessel when catheter manipulations are performed. The dilator 510 is a device which is inserted into a sheath lumen when the introducer sheath 500 is to be introduced into a blood vessel and is removed after it is integrated with the sheath lumen and inserted into the blood vessel. The dilator 510 has a lumen for a guide wire. The guide wire holder tube 520 is a packaging tube for protecting a guide wire 530 and need not itself be primed. However, it may be desirable to inject fluid into the lumen of the guide wire holder tube 520 to wet the surface of the guide wire 530.

Figure 7:
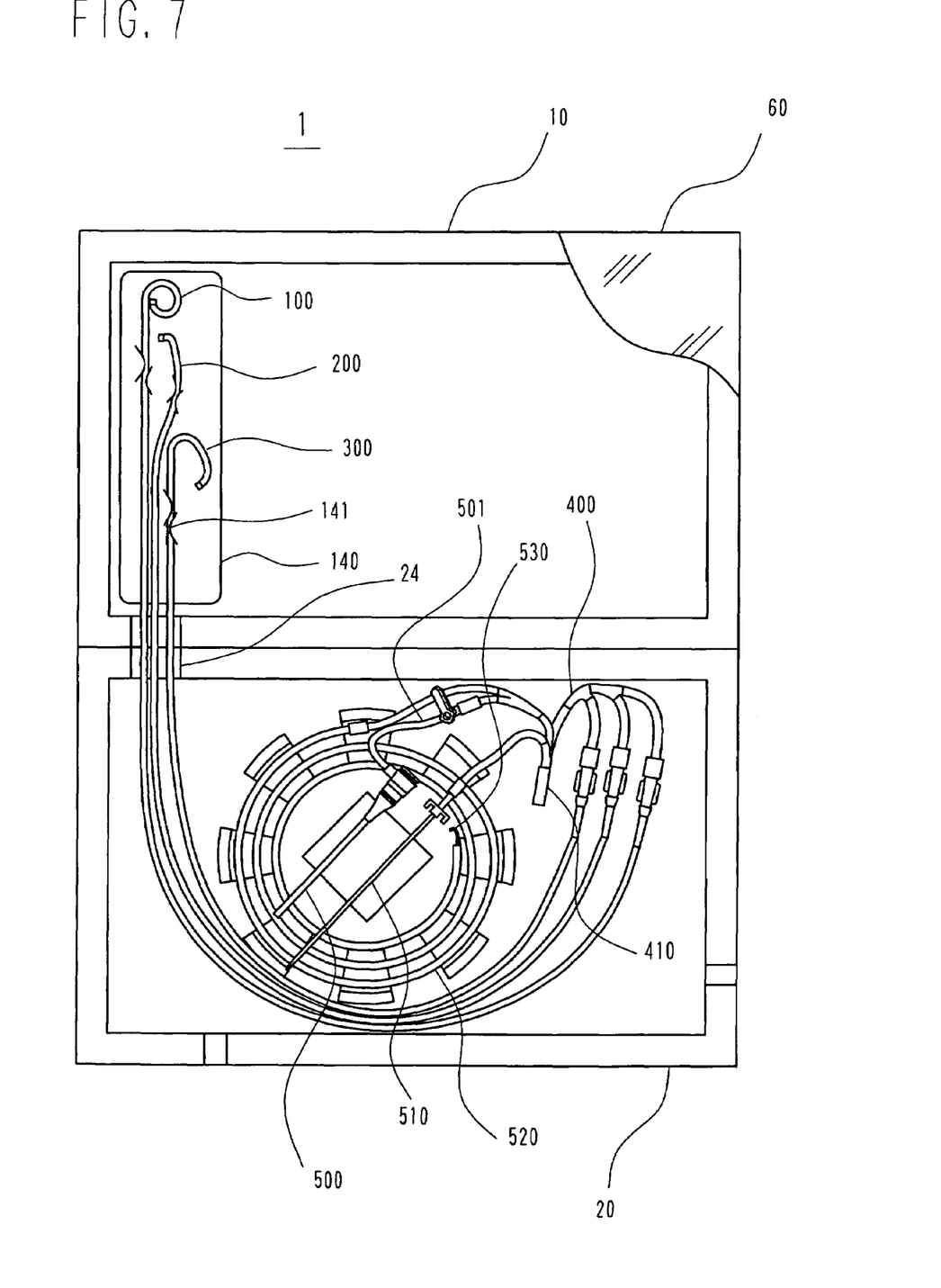
FIG. 7 is a top view of another medical device accommodating tray according to an embodiment of the present invention in which a plurality of medical tubes are disposed in the tray.

FIG. 7 shows another embodiment of the present invention. This embodiment differs from the first embodiment described above in that the branching member is in the form of a branching tube 400. Thus, instead of using the manifold with three-way cocks as the branching member, the embodiment shown in FIG. 7 uses a branching tube which does not have a plurality of three-way cocks. The branching member in the form of the branching tube 400 includes a plurality of branched flow paths connected individually to the medical tubes. The branched flow paths each possess an orifice defining an inner diameter of the flow path. In the illustrated version of the branching tube, a total of six medical tubes are individually connected to the branching tube so that each branched flow path of the branching tube is in fluid communication with one of the medical tubes. The six medical tubes include not only the catheters 100, 200, 300, but also an introducer sheath 500, a dilator 510 and a guide wire holder tube 520 in which a guide wire 530 is placed.

In FIG. 7, the branching tube 400 is provided with a connecting portion 410 that is adapted to be connected to the syringe 50. In the illustrated embodiment, the connecting portion 410 is formed by the proximal end of the branching tube 400. The branching tube 400 includes a plurality of branching portions, each possessing an end portion (distal end portions of the branching tube) connected to a connector provided at each of the medical tubes respectively. With respect to the introducer sheath 500, a branching portion 501 with a three-way cock is connected as a connector. This is because a valve for preventing flowing out of the blood is built in at a proximal end portion of the introducer sheath 500.

The medical tubes mentioned above have lumens which possess different flow path cross-sectional areas relative to one another. The medical tubes thus exhibit different injection resistances from each other upon priming. Further, because the medical tubes possess total lengths differing from one another, the volume (priming volumes) for accepting the fluid in the lumen of the various medical tubes are different from each other. Therefore, in the present embodiment, each of the branched flow paths connected individually to the medical tubes has an orifice which defines an inner diameter of the flow path, and the orifices possess different sectional areas (cross-sectional areas) at the connecting portions of the branching tube 400.

In the present embodiment, the flow path sectional area of each of the orifices in the branching tube 400 is designed such that it increases in proportion to the priming volume of the corresponding medical tube and is at least as small as (or smaller than) the sectional area of that one of the lumens of the medical tubes which has the smallest sectional area. Since the flow path sectional area of each orifice is designed so as to increase in proportion to the priming volume of the corresponding medical tube, the priming operations of the medical tubes can be ended at the same time. Further, the reason that the flow path sectional area of each orifice is designed to be smaller than the sectional area of that one of the lumens of the medical tubes which has the smallest sectional area is that, if the sectional area of any orifice is greater than the sectional area of the lumen, the injection resistance is controlled by the sectional area of the lumen.

Preferred values for the flow path sectional area, length and priming volume of particular medical tubes and the sectional area of orifices to be connected to the medical tubes are indicated in Table 1 below.

In Table 1, the greatest priming volume is 3.9 ml for the guide wire holder tube 520. Meanwhile, the medical tube possessing the smallest lumen sectional area is the angiographic catheter whose lumen sectional area is 0.014 cm$^2$. Accordingly, the sectional area of the orifice for the guide wire holder tube 520 which exhibits the greatest priming volume is 0.014 cm$^2$ and the sectional area of the orifice for the other medical tubes is set so that the ratio of the priming volume of the medical tube to the orifice sectional area coincides with the ratio (3.9:0.014). This ratio corresponds to the ratio of the priming volume of the guide wire holder tube 520 to the sectional area of the orifice of the guide wire holder tube 520.

By determining the sectional area of the orifices in this manner, the injection resistance is not influenced by the sectional area of the lumen of the medical tube as might otherwise be the case. The priming operations of the medical tubes can be accomplished substantially at the same time by a single operation. It is to be understood that this same aspect can be applied to the branching member shown in FIG. 4 if such branching member/manifold is used in connection with medical tubes other than angiographic catheters which possess different cross-sectional areas and/or priming volumes. Thus, the flow paths in the manifold that are individually connected to the medical tubes can be provided with orifices having different cross-sectional areas as described above.

TABLE 1

| Medical tube type | Lumen sectional area (cm²) | Length (cm) | Priming amount (ml) | Orifice sectional area (cm²) |
|---|---|---|---|---|
| Dilator | 0.02 | 10 | 0.2 | 0.000718 |
| Introducer sheath | 0.1 | 10 | 1.0 | 0.00359 |
| Angiographic Catheter, JR shape | 0.014 | 100 | 1.4 | 0.005026 |
| Angiographic Catheter, JL shape | 0.014 | 100 | 1.4 | 0.005026 |
| Angiographic Catheter, pigtail shape | 0.014 | 110 | 1.5 | 0.005385 |
| Guide wire holder tube (except guide wire sectional area) | 0.026 | 150 | 3.9 | 0.014 |

While preferred embodiments of the present invention have been described using specific terms, such description is for illustrative purposes only. It is to be understood that changes and variations may be made, and equivalents employed, without departing from the spirit or scope of the invention as defined by the claims.

What is claimed is:

1. A package for medical tubes comprising:
a holder having an aseptic interior in which is positioned a plurality of medical tubes;
each of the plurality of medical tubes comprising a tube body possessing a tube wall defining a lumen extending between a distal end portion of the medical tube and a proximal end portion of the medical tube; and
a branching member to which is connected each of said plurality of medical tubes, said branching member comprising a plurality of branched flow paths each fluidly communicating with the lumen of one of said plurality of medical tubes, wherein
at least one of the plurality of medical tubes is configured to be inserted into a blood vessel.

2. The package for medical tubes according to claim 1, wherein said plurality of medical tubes comprises at least one of an angiographic catheter, a guiding catheter, an introducer sheath, a dilator and a guide wire holder tube.

3. The package for medical tubes according to claim 2, wherein each of said plurality of medical tubes possesses a connector that is connected to the branching member.

4. The package for medical tubes according to claim 1, wherein each of said branched flow paths comprises an orifice in fluid communication with one of the lumen and possessing an orifice flow path cross-sectional area, each of the lumens possessing a lumen flow path cross-sectional area, the orifice flow path cross-sectional area of each orifice being no greater than the lumen flow path cross-sectional area of the lumen which possesses a smallest lumen flow path cross-sectional area.

5. The package for medical tubes according to claim 4, wherein the orifice flow path sectional area of each respective orifice is proportional to a priming volume of the lumen of the medical tube which is connected to the respective orifice.

6. The package for medical tubes according to claim 1, wherein each of said branched flow paths comprises an orifice in fluid communication with one of the lumens and possessing an orifice flow path cross-sectional area, each of the lumens possessing a lumen flow path cross-sectional area, the lumen of each medical tube possessing a priming volume, and wherein for each respective lumen and the orifice to which the respective lumen is fluidly communicated, there exists a ratio of the priming volume of the lumen to the orifice flow path sectional area of the orifice, said ratio being the same for each respective lumen and the orifice to which the respective lumen is fluidly communicated.

7. A package for medical tubes comprising:
a holder possessing an interior under aseptic conditions;
a plurality of medical tubes positioned in the interior of the holder;
each of the plurality of medical tubes comprising a tube body possessing a distal end portion, a proximal end portion, and a tube wall surrounding a lumen that extends between the distal end portion and the proximal end portion; and
a branching member positioned in the interior of the holder;
the branching member comprising a plurality of flow paths each adapted to be fluidly connected to the lumen of one of the medical tubes to fluidly communicate the flow path with the lumen of the medical tube, the branching member also comprising a main adapter adapted to fluidly communicate with the plurality of flow paths so that priming fluid introduced into the main adapter can flow to the flow paths and into the lumen of each medical device that has been fluidly connected to one of the flow paths, wherein
said plurality of medical tubes comprises more than one of an angiographic catheter, a guiding catheter, an introducer sheath, a dilator and a guide wire holder tube.

8. The package for medical tubes according to claim 7, wherein each of said plurality of medical tubes possesses a connector that is adapted to be connected to the branching member.

9. The package for medical tubes according to claim 7, wherein each of said flow paths comprises an orifice possessing an orifice flow path cross-sectional area, each of the lumens possessing a lumen flow path cross-sectional area, the orifice flow path cross-sectional area of each orifice being no greater than the lumen flow path cross-sectional area of the lumen which possesses a smallest lumen flow path cross-sectional area.

10. The package for medical tubes according to claim 7, wherein the holder comprises at least one tray having a bottom surface and upstanding side walls, and cover sealed to the tray.

11. The package for medical tubes according to claim 10, wherein the tray comprises a plurality of upstanding projections on the bottom surface.

12. The package for medical tubes according to claim 7, wherein said plurality of medical tubes comprises an angiographic catheter, a guiding catheter, an introducer sheath and a dilator.

13. A package for medical tubes comprising:
a tray having a bottom and an upstanding peripheral wall;
a cover sealed to the tray to define together with the bottom and the upstanding peripheral wall an aseptic interior;
a plurality of medical tubes positioned in the aseptic interior of the tray;
a branching member positioned within the aseptic interior of the tray;
each of the plurality of medical tubes comprising a tube body possessing a distal end portion, a proximal end portion, and a tube wall surrounding a lumen that extends between the distal end portion and the proximal end portion; and
the branching member comprising a plurality of flow paths each fluidly connected to the lumen of a respective one of the medical tubes to fluidly communicate each flow path with the lumen of the respective medical tube.

14. The package for medical tubes according to claim 13, wherein said plurality of medical tubes comprises at least three catheters.

15. The package for medical tubes according to claim 13, wherein said branching member is a manifold comprising a plurality of stopcocks, each of said plurality of medical tubes being connected to one of the stopcocks.

16. The package for medical tubes according to claim 13, wherein said branching member is a branching tube comprising a plurality of branching portions each connected to one of said plurality of medical tubes.

17. A method for priming a plurality of medical tubes comprising:
   introducing fluid from a fluid source into a branching member that is connected to a plurality of medical tubes, the branching member comprising a plurality of branched flow paths and each of the plurality of medical tubes comprising a tube wall surrounding a lumen, each of the branched flow paths of the branching member being in fluid communication with the lumen of one of the plurality of medical tubes; and
   the fluid introduced into the branching member flowing to the plurality of branched flow paths and into the lumen of each of the medical tubes to fill the lumen of each of the medical tubes with the fluid.

18. The method according to claim 17, wherein the plurality of medical tubes and the branching member are packaged in a sealed package possessing an interior that is under aseptic conditions, the method further comprising opening said sealed package prior to introducing fluid into said branching member.

19. The method according to claim 18, further comprising removing said plurality of medical tubes from said package after the lumen of each respective medical tube has been filled with the fluid.

20. The method according to claim 17, wherein the plurality of medical tubes and the branching member are packaged in a tray to which is sealed a cover to provide an interior that is under aseptic conditions, the tray comprising a bottom and an upstanding peripheral wall, the method further comprising removing said cover prior to introducing fluid into said branching member.

21. The method according to claim 20, further comprising removing said plurality of medical tubes from said tray after the lumen of each respective medical tube has been filled with the fluid.

22. The method according to claim 17, further comprising disconnecting said plurality of medical tubes from said branching member after the lumen of each respective medical tube has been filled with the fluid.

23. The method according to claim 17, wherein the fluid is introduced into a manifold forming the branching member, said manifold comprising a plurality of stopcocks.

24. The method according to claim 17, wherein said plurality of medical tubes comprise at least one of an angiographic catheter, a guiding catheter, an introducer sheath, a dilator and a guide wire holder tube.

25. The method according to claim 17, wherein said plurality of medical tubes comprise an angiographic catheter, a guiding catheter, an introducer sheath and a dilator.

26. The method according to claim 17, wherein the fluid is introduced into a branching tube forming the branching member.

* * * * *